US012654038B2

(12) United States Patent
Sato et al.

(10) Patent No.: US 12,654,038 B2
(45) Date of Patent: Jun. 16, 2026

(54) CRANIAL ACOUSTIC COUPLING APPARATUS AND METHODS

(71) Applicant: Sanmai Technologies, PBC, Sunnyvale, CA (US)

(72) Inventors: Tomokazu Sato, Minneapolis, MN (US); Christopher Daft, Tucson, AZ (US); Timothy Mullen, Hidden Meadows, CA (US)

(73) Assignee: Sanmai Technologies, PBC, Sunnyvale, CA (US)

( * ) Notice: Subject to any disclaimer, the term of this patent is extended or adjusted under 35 U.S.C. 154(b) by 0 days.

(21) Appl. No.: 18/782,487

(22) Filed: Jul. 24, 2024

(65) Prior Publication Data

US 2025/0032822 A1 Jan. 30, 2025

Related U.S. Application Data

(60) Provisional application No. 63/607,032, filed on Dec. 6, 2023, provisional application No. 63/516,463, filed on Jul. 28, 2023, provisional application No. 63/516,465, filed on Jul. 28, 2023, provisional application No. 63/516,469, filed on Jul. 28, 2023.

(51) Int. Cl.
*A61N 7/00* (2006.01)
*A61B 5/00* (2006.01)
*A61N 7/02* (2006.01)

(52) U.S. Cl.
CPC .............. *A61N 7/00* (2013.01); *A61B 5/7203* (2013.01); *A61N 7/02* (2013.01); *A61N 2007/0026* (2013.01); *A61N 2007/0078* (2013.01)

(58) Field of Classification Search
CPC .... A61N 7/00; A61N 2007/0021; A61B 5/28; A61B 5/291
See application file for complete search history.

(56) References Cited

U.S. PATENT DOCUMENTS

| | | |
|---|---|---|
| 5,273,037 A | 12/1993 | Itil et al. |
| 5,590,653 A | 1/1997 | Aida et al. |
| 6,236,875 B1 * | 5/2001 | Bucholz ................. A61B 6/501 600/407 |

(Continued)

FOREIGN PATENT DOCUMENTS

| | | |
|---|---|---|
| CN | 108652670 A | 10/2018 |
| WO | 2023/278199 A1 | 1/2023 |

OTHER PUBLICATIONS

"Electronically Programmable, Reversible Shape Change in Two- and Three-Dimensional Hydrogel Structures" by C. Yu et al. Advanced Materials. 2013, 25, pp. 1541-1546 (Year: 2013).*

(Continued)

*Primary Examiner* — Jason M Ip
(74) *Attorney, Agent, or Firm* — Artegis Law Group, LLP

(57) ABSTRACT

Cranial acoustic coupling apparatuses and methods to improve coupling to the head for use in transcranial focused ultrasound systems (tFUS) are disclosed. The apparatuses are constructed using multiple components and layers to reduce the air gaps due to head curvature and smaller-scale features such as dimples, hair, and so on. An apparatus or system can include a holder unit and an attachment puck. The holder unit can include one or more ultrasound transducers. The attachment puck can include an attachment layer that interfaces with a head.

25 Claims, 9 Drawing Sheets

600

(56) References Cited

U.S. PATENT DOCUMENTS

| | | | |
|---|---|---|---|
| 10,413,757 B2 | 9/2019 | Sato et al. | |
| 11,266,378 B1 | 3/2022 | Peeters et al. | |
| 11,458,337 B2 | 10/2022 | Ebbini et al. | |
| 11,596,812 B2 | 3/2023 | Ebbini | |
| 11,672,986 B2 | 6/2023 | Opie et al. | |
| 2005/0201574 A1* | 9/2005 | Lenhardt | A61H 23/0245 |
| | | | 381/151 |
| 2006/0184070 A1* | 8/2006 | Hansmann | A61N 7/00 |
| | | | 601/2 |
| 2008/0021353 A1* | 1/2008 | Menzi | A61B 17/2251 |
| | | | 601/1 |
| 2008/0177221 A1 | 7/2008 | Millerd et al. | |
| 2009/0299235 A1 | 12/2009 | Babaev | |
| 2012/0289869 A1* | 11/2012 | Tyler | A61N 7/00 |
| | | | 601/2 |
| 2014/0316269 A1 | 10/2014 | Zhang et al. | |
| 2016/0038770 A1 | 2/2016 | Tyler et al. | |
| 2016/0143541 A1 | 5/2016 | He et al. | |
| 2016/0302765 A1* | 10/2016 | Liu | A61B 8/4281 |
| 2018/0140871 A1 | 5/2018 | Konofagou et al. | |
| 2020/0121960 A1 | 4/2020 | Darrow et al. | |
| 2021/0346726 A1 | 11/2021 | Kiani | |
| 2021/0353967 A1 | 11/2021 | Yu et al. | |
| 2022/0167868 A1 | 6/2022 | Sela et al. | |
| 2022/0193455 A1 | 6/2022 | Thyagarajan | |
| 2022/0193456 A1 | 6/2022 | Thyagarajan | |
| 2022/0197383 A1 | 6/2022 | Thyagarajan | |
| 2023/0082109 A1* | 3/2023 | Ramamurthy | A61B 8/0808 |
| | | | 600/459 |
| 2023/0166129 A1 | 6/2023 | Murphy et al. | |
| 2023/0190185 A1 | 6/2023 | Dvorak et al. | |
| 2023/0191127 A1 | 6/2023 | Kadosh et al. | |
| 2023/0210493 A1 | 7/2023 | Kubanek | |
| 2024/0008847 A1 | 1/2024 | Segre et al. | |
| 2024/0050761 A1* | 2/2024 | Gurfein | A61N 2/006 |

OTHER PUBLICATIONS

"Heating Induced by Therapeutic Ultrasound in the Presence of Magnetic Nanoparticles" by K. Kaczmarek et al. Applied Materials and Interfaces. vol. 10, Issue 14, Mar. 2018 (Year: 2018).*

"Real-time integration of ultrasound into neuronavigation: technical accuracy using a light-emitting-diode-based navigation system" by A. Jodicke et al. Acta Neurochir. 1211-1220. 2004.*

Non Final Office Action received for U.S. Appl. No. 18/782,472, dated Oct. 6, 2025, 18 pages.

Non Final Office Action received for U.S. Appl. No. 18/783,245, dated Nov. 10, 2025, 34 pages.

Allard et al., "MRI Guided Transcranial Acoustoelectric Imaging for Safe and Accurate Electrical Brain Mapping", IEEE International Ultrasonics Symposium, DOI: 10.1109/IUS54386.2022. 9958749, Oct. 2022, pp. 1-4.

Final Office Action received for U.S. Appl. No. 18/782,472, dated Jan. 30, 2026, 25 pages.

Final Office Action received for U.S. Appl. No. 18/383,245, dated Apr. 29, 2026, 20 pages.

* cited by examiner

CRANIAL ACOUSTIC COUPLING APPARATUS AND METHODS

CROSS-REFERENCE TO RELATED APPLICATIONS

This application claims priority to and the benefit of U.S. Provisional patent application titled, "APPARATUS COMPATIBLE WITH PHYSIOLOGICAL MEASUREMENT SYSTEMS AND ULTRASOUND BEAM GUIDANCE FOR NEURO NAVIGATION," filed on Jul. 28, 2023, and having Ser. No. 63/516,463, U.S. Provisional patent application titled, "SHIELDING TECHNIQUES FOR APPARATUS COMPATIBLE WITH PHYSIOLOGICAL MEASUREMENT SYSTEMS AND ULTRASOUND BEAM GUIDANCE," filed on Jul. 28, 2023, and having Ser. No. 63/516,465, U.S. Provisional patent application titled, "APPARATUS COMPATIBLE WITH PHYSIOLOGICAL MEASUREMENT SYSTEMS AND ULTRASOUND BEAM GUIDANCE CONFIGURED WITH ULTRASOUND AND EEG POSTS," filed on Jul. 28, 2023, and having Ser. No. 63/516,469, and U.S. Provisional patent application titled, "CRANIAL ACOUSTIC COUPLING APPARATUS AND METHODS," filed on Dec. 6, 2023, and having Ser. No. 63/607,032. The subject matter of these related application are hereby incorporated herein by reference.

BACKGROUND

Field of the Various Embodiments

This disclosure relates to coupling transcranial focused ultrasound systems (tFUS) to the scalp using cranial acoustic coupling apparatuses and methods.

DESCRIPTION OF THE RELATED ART

Transcranial focused ultrasound (tFUS) systems help treat several types of mental illness using low-intensity ultrasound (US). Ultrasound gels or couplants allow the US waves to pass into the body without getting distorted by the air between the body and the ultrasound transducer or probe. tFUS systems have a unique challenge with air gaps due to the curvature of the scalp, hair, dimples, etc. The scalp is harder than a more elastic surface like the abdomen, where pressing the ultrasound probe closer to the skin makes it easier to eliminate air gaps. One drawback of current systems is that gels can be messy because they can drip onto the face, eyes, ears, etc., making the experience unpleasant. This is further complicated because cleaning the gel from the scalp and hair is harder. Most of the tFUS systems are targeted for use in a clinical setting; the messiness of using the couplant and the cumbersome cleanup prevents the use of tFUS at home. There needs to be better tFUS couplant techniques and apparatus that are easier to use.

SUMMARY

One embodiment of the present disclosure sets forth a system that includes: a holder unit that includes one or more ultrasound transducers; and an attachment puck that includes at least one layer configured to interface with a surface of a head.

At least one technical advantage of the disclosed techniques relative to the prior art is that, with the disclosed techniques, multiple components and layers can provide improved sealing and compliance in relation to gaps between the device and skull or head surface geometry as well as smaller-scale features such as dimples, hair, etc. For example, an attachment puck can detachably attach to a holder unit, so that the interface components can be fresher than examples that do not include a detachable puck system. This can improve coupling, reduce mess, and provide easier clean-up relative to existing technologies. These technical advantages provide one or more technological advancements over prior art approaches.

One embodiment of the present disclosure sets forth a method that includes providing a holder unit that includes one or more ultrasound transducers; and holding, using the holder unit, an attachment puck configured to interface with a head (e.g., head surface).

At least one technical advantage of the disclosed techniques relative to the prior art is that, with the disclosed techniques, multiple components and layers can provide improved sealing and compliance in relation to gaps between the device and skull geometry as well as smaller-scale features such as dimples, hair, etc. For example, an attachment puck can detachably attach to a holder unit, so that the interface components can be fresher than examples that do not include a detachable puck system. This can improve coupling, reduce mess, and provide easier clean-up relative to existing technologies. These technical advantages provide one or more technological advancements over prior art approaches.

One embodiment of the present disclosure sets forth an apparatus that includes: a holder unit that includes one or more ultrasound transducers; and an attachment puck that includes an attachment layer configured to interface with a surface of a head.

At least one technical advantage of the disclosed techniques relative to the prior art is that, with the disclosed techniques, multiple components and layers can provide improved sealing and compliance in relation to gaps between the device and skull geometry as well as smaller-scale features such as dimples, hair, etc. For example, an attachment puck can detachably attach to a holder unit, so that the interface components can be fresher than examples that do not include a detachable puck system. This can improve coupling, reduce mess, and provide easier clean-up relative to existing technologies. These technical advantages provide one or more technological advancements over prior art approaches.

These technical advantages provide one or more technological advancements over prior art approaches.

BRIEF DESCRIPTION OF THE DRAWINGS

So that the manner in which the above recited features of the various embodiments can be understood in detail, a more particular description of the inventive concepts, briefly summarized above, can be had by reference to various embodiments, some of which are illustrated in the appended drawings. It is to be noted, however, that the appended drawings illustrate only typical embodiments of the inventive concepts and are therefore not to be considered limiting of scope in any way, and that there are other equally effective embodiments.

DETAILED DESCRIPTION

Cranial acoustic coupling apparatuses and methods to improve transcranial focused ultrasound systems (tFUS) and/or EEG coupling in relation to a surface of a head. A surface of a head can include the scalp, forehead, temples, and so on. The surface of the head can refer to the surface whether hair, oil, blemishes, and other features are present in relation to the head. In some examples, the term head or human head can refer to any surface of the head. The apparatuses are constructed using multiple components and layers to reduce the air gaps due to skull curvature and smaller-scale features such as dimples, hair, etc. Liquids or gels with physical properties that can be tuned to improve coupling, mess-free application, and easier clean-up are used. Gaskets or O-rings are used to improve the sealing with the head in an implementation. Fluid bags are used in a different implementation. Some of the layers of coupling apparatus are reusable or capable of being refurbished. Techniques using pressure and vacuum to improve coupling are used. A method to improve coupling using a customized coupling apparatus is described.

An ultrasound transducer sends and receives ultrasound waves. The term "holder unit" (also referred to as the core puck here) here refers to part of a transducer coupling apparatus that holds the transducer. The holder unit and its components can transmit and receive ultrasound energy between the transducer (or transducer array) and the human head (e.g, scalp, forehead, and other surfaces with or without hair). Generally, the holder unit can hold a replaceable attachment puck (or alternatively can include a permanent surface) that conforms to the human head and effectively eliminate air bubbles or pockets in the path of the ultrasound waves. The overall transducer coupling apparatus can include multiple components and layers. Prior art solutions typically use a layer of gel or other solutions that act as the final layer. As described, gels are messy, and cleanup is challenging. This application discloses techniques and apparatuses with several usability features:

Effective ultrasound coupling to the head:
Easy and effective coupling
Preventing air gaps due to macroscopic curvature of the skull and smaller-scale features such as dimples, hair, etc.
Reduction of mess while using tFUS systems
Easier clean up after use
Reducing waste by reusing or refurbishing pucks.

Figure 1A:
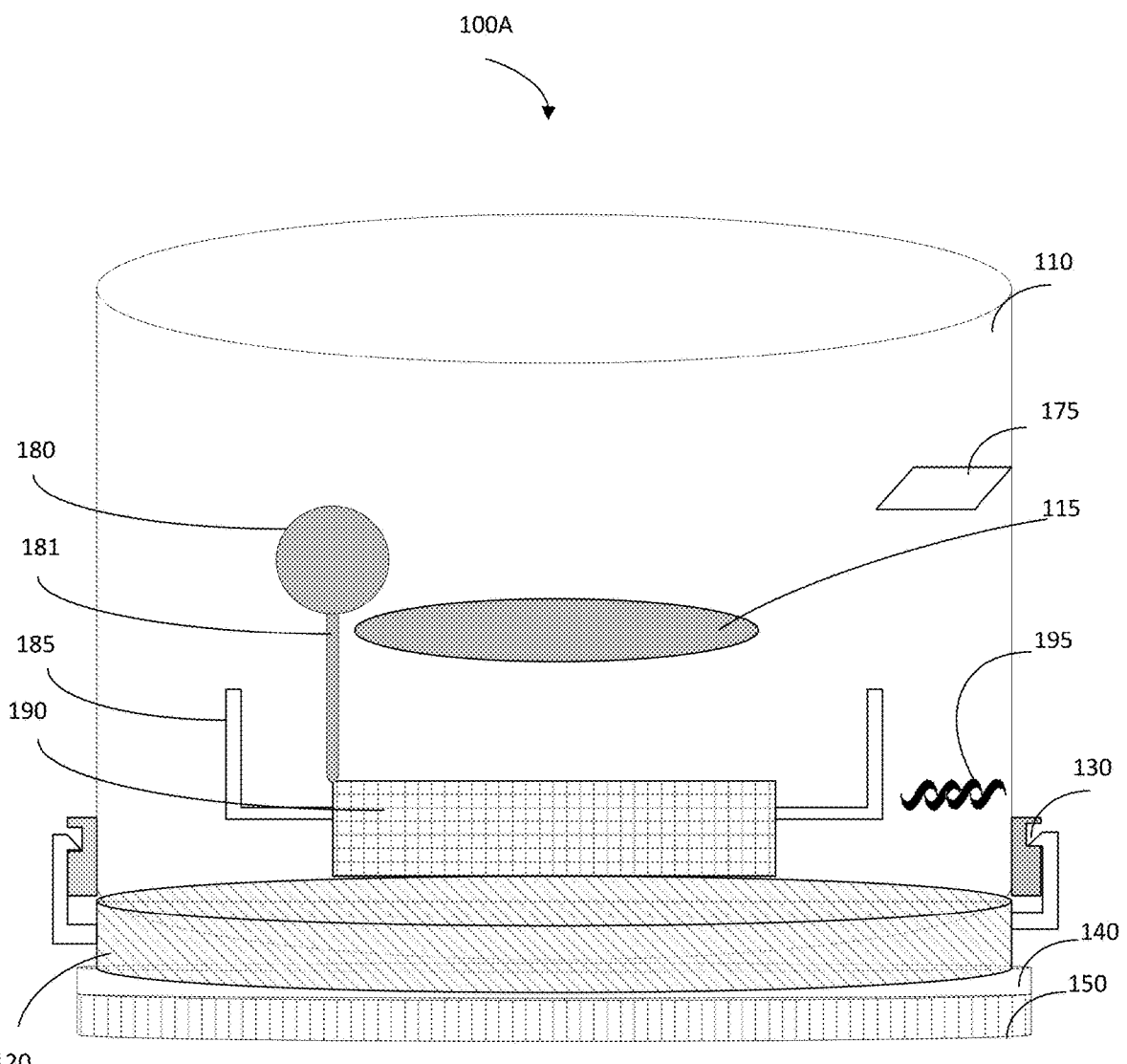
FIGS. 1A-1C show examples of transducer coupling systems according to various embodiments.
Figure 1B:
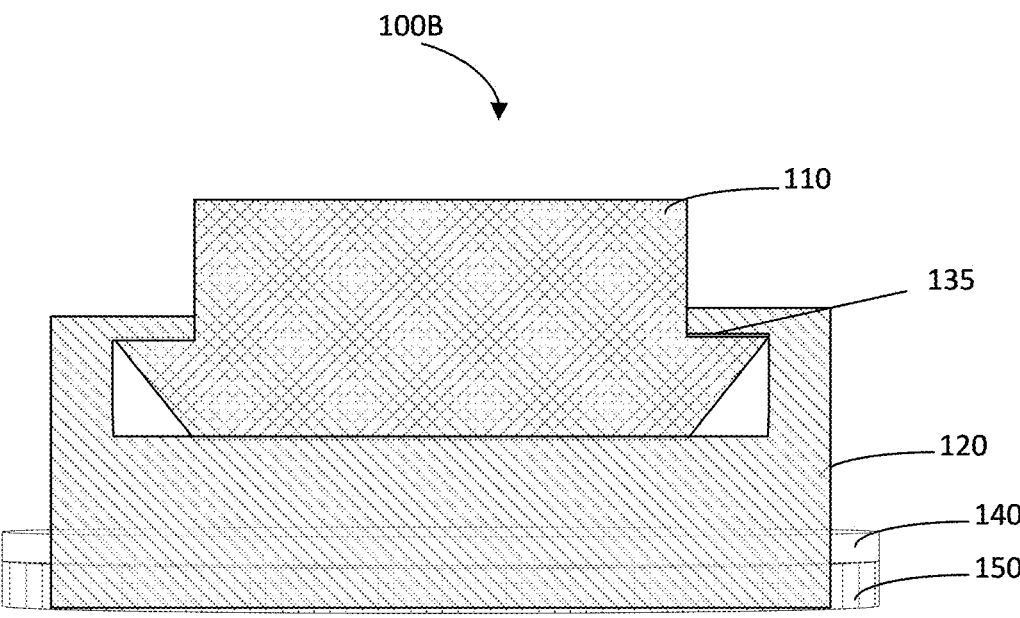
Figure 1C:
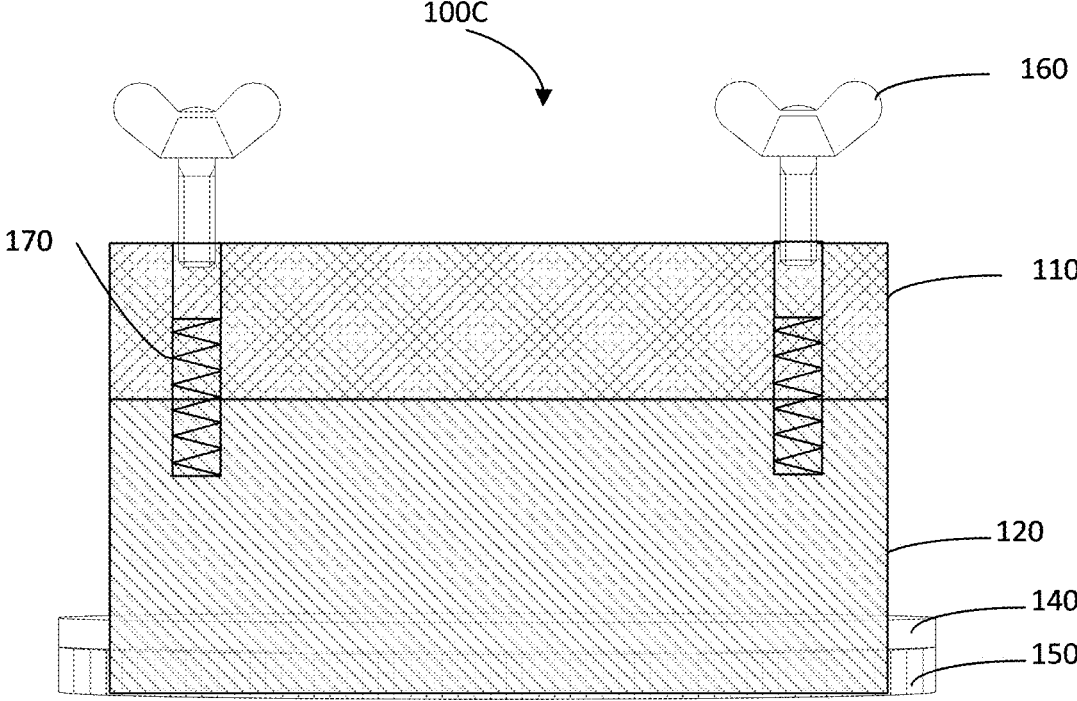

FIGS. 1A-1C show examples of transducer coupling assembly unit or system implementations. The figures in this document are for illustrative purposes only. The figures are not intended to be presented to scale or location-accurate.

FIG. 1A shows transducer coupling assembly or system 100A is circular. However, in other implementations the transducer coupling system 100A can be rectangular (see FIG. 1B and FIG. 1C), elliptical, curved, or composed of many different geometrically shapes to conform to the surface of the head better. Referring to FIG. 1A, transducer coupling system 100A includes holder unit 110. Embedded with the plastic housing of holder unit 110 is at least one transducer 115 (or transducer array). Transducer 115 generates and receives ultrasound waves for skull characterization, guidance, and tFUS stimulation. In an embodiment, the holder unit 110 includes at least one physiological measurement device, such as an electroencephalogram (EEG) system with its electrodes (not shown). Feedback identified using the EEG device can be used to monitor efficacy and move the puck or holder into a position that improves ultrasound efficacy, EEG efficacy, or any combination thereof. The physiological measurement device can be used to monitor the efficacy of the treatment.

Included within holder unit 110 are one or more LEDs, indicators (for displaying status and neuronavigational indicia), as well as neuronavigational guides and markers 175. LEDs can also be used to affect properties of liquids or gels delivered using the device. In an implementation, at least one Mesh 190, which is electrically and thermally conductive, is used for electrical noise elimination in an operation similar to a faraday cage. The mesh 190 can connect to one or more electrodes 185. When current passes through mesh 190, it can be used for heating. In a different implementation, Mesh 190 is connected to conducting channels (or metal rods) 181, which are connected to a Peltier cooler 180 to make a cooling mesh. As a result, a mesh 190 can be used for thermo-management including heating, cooling, or any combination thereof. In yet another implementation, electrodes 185 create an electrical potential difference that affects hydrogel properties (electrorheological). One or more electromagnets 195 are used to effect magnetic nanoparticles in a different implementation. Holder unit 110 includes the necessary electronics for control. In an embodiment, holder unit 110 includes means for generating a mechanical force to affect the viscosity of materials (non-Newtonian fluids) via ultrasound array or normal auditory range or sub-hearing range buzzers. This ultrasound array can be different from transducer array 115 illustrated and described.

While the components mentioned above, such as meshes, can be included in the core puck 110, they can also be implemented in the attachment puck 120.

An attachment puck 120 is attached to holder unit 110 using clasp 130. Attachment puck 120 describes a set of components attached to the core puck 110 to improve coupling, make it mess-free to use, and make it easier to clean up. Various attachment pucks can be further distinguished on whether they might be used or reused:

Reusable components can refer to attachment pucks 120, holder units 110, and other portions of a transducer coupling system 100 that can be used multiple times but are not expected to have an indefinite lifetime. Thus, they can be rated for certain hours, cycles, or usage times.

Refurbishable components can refer to attachment pucks 120, holder units 110, and other portions of a transducer coupling system 100 that can be made to work again for a certain number of cycles using some procedures, such as microwaving or cooling, submersion in a water bath, etc.

Reusable and refurbishable components are not necessarily mutually exclusive, and many designs are meant to enhance both aspects.

Disposable components can refer to attachment pucks 120, holder units 110, and other portions of a transducer coupling system 100 meant for one-time use.

Attachment puck 120 is attached to holder unit 110 using connection devices such as the clasp 130 (FIG. 1A), the snap-fit device 135 (FIG. 1B), screw connector 160 (FIG. 1C), or other means such as double-sided adhesive. Attachment puck 120 can contain fluids such as liquids or gels. Gels can include hydrogels, aerogels, and so on. Fluids can be contained in a fluid bag. Attachment pucks 120 can include one or more channels allowing small amounts of gel or liquid to seep onto the surface of the head. The channels can be located under array 115. In an implementation, attachment puck 120 is filled with a pre-cooled gel. Gels or liquids are doped with magnetic nanoparticles in an implementation. In a different implementation, gels or liquids are doped with statically charged particles.

This application discloses an attachment puck 120 that can maintain better coupling to the surface of the head, including gaskets/O-rings, suction/vacuum, adhesion, and springs/screws. Note that some aspects, such as vacuums, will be described here as a method to reduce detachment of the attachment puck 120 and overall transducer coupling system 100 from the surface of the head, as opposed to a method for releasing and recapturing gels used in the tFUS system. Thus, the goals are different. However, the physical implementation of the two can, in some examples, be similar or identical. Also, note that the vacuum does not necessarily refer to a constant vacuum source. A pulled syringe with negative pressure can be considered a practical vacuum source.

FIG. 1B shows transducer coupling system 100B, which is similar to transducer coupling system 100A shown in FIG. 1A, with the difference that transducer coupling system 100B is rectangular and uses a snap-fit 135 instead of clasp 130. Although FIG. 1B does not show all the features (Mesh 190, Peltier cooling 180, cooling rod 181, electrodes 185, markers/LED 175, electromagnets 195, and transducer 115) in FIG. 1A, transducer coupling system 100B and/or attachment puck 120 can still include them.

Springs and Screws

FIG. 1C shows transducer coupling system 100C is similar to transducer coupling system 100B of FIG. 1B and the transducer coupling system 100A of FIG. 1A, except that transducer coupling system 100C uses screws 160 instead of a snap-fit to attach attachment puck 120 to holder unit 110. In an implementation, screws 160 can be used primarily for applying pressure, and a snap-fit, adhesive tape, or clasp is used as a primary attachment component for attaching attachment puck 120 to holder unit 110. Transducer coupling system 100C includes one or more springs 170 and corresponding screws 160. Springs 170 and screws 160 can apply controlled pressure. This can be used to squeeze out air gaps or have a controlled amount of release from gel bags and other intermediate components. Release of this mechanical pressure can also pull the gels back into the bag if the bag has elastic properties. Screws can mainly be used for stable angling of the transducer 115 components relative to the skull. Springs alone may not work as well since while they can be helpful to hold a flat surface flush against another flat surface, they would have too much wobble and freedom of motion by themselves in a scenario with curved surfaces. In an implementation, multiple sets of screws and springs can be used to secure the attachment puck 120 to holder unit 110 and apply pressure.

Gaskets or O-rings

A gasket or O-ring 140, in some examples with an adhesive surface layer 150, can form a tight seal with the surface of the head. While the surface of the head can have too much lateral motion for this to be used as a primary mechanism of maintaining the aim of the ultrasound, it helps prevent decoupling or detachment from the surface of the head and subsequent air gaps and loss of effective ultrasound transmission. The spring and screws can also apply force onto these gaskets to further improve sealing.

In one implementation, the gasket 140 portion can be reusable, and upon each use, a new double-sided, waterproof adhesive sticky ring 150 is applied.

In another implementation, attachment puck 120 includes or consists of gasket 140 in a mold, and a molten hydrogel is poured. This mold (complete with gasket and hydrogel) is frozen or cooled to solidify.

The solidified attachment puck 120 can be attached to the holder unit 110 and secured to the surface of the head (along with proper ultrasound targeting). The central portion of solidified attachment puck 120 can be returned to a gel state using heat (for example, body temperature, heating elements (MESH 190), or a hair dryer). In this way, the gasket seal is already formed, and the targeting is done, resulting in less mess and lesser usage of liquids and gels. In a further implementation, a gasket 140 in a mold with molten hydrogel can be placed on the surface of the head and then frozen or cooled using Peltier cooling 180 and cooling rod 181. For example, the hydrogel can melt around the temperature of the surface of the head while it is relatively solid (free of liquid dripping) at room temperature. In such a case, freezing or cooling using a Peltier cooler can be omitted. However, additional cooling and heating methods can be used if suitable melting property gels are unavailable. For example, if the gel is still too liquid for "mess-free" application at room temperature, it can be pre-cooled with cooling maintained with a Peltier system. If a gel is still not liquid enough at head temperature, it can be gently heated (similar to the temperatures in a sauna or a hair dryer) to have a liquid interface. The system can include temperature regulation systems that regulate a temperature of the liquids and gel to a target temperature that is associated with the particular liquid, gel, or other fluid being utilized, thereby reducing mess while maintaining efficacy.

A benefit provided by some embodiments is that the ultrasound can travel through acoustically-matched media to soft tissue. This implies the same speed of sound and the same density of soft tissue, especially the head. However, if the acoustic impedance is well-matched, while sound propagation may have some refractive effects, reflected and wasted ultrasound energy can be minimized or reduced. The refractive effects can be reduced or corrected with thin layers and layers with predetermined geometries. Silicone and hydrogels can be used to highlight two examples of such acoustically-matched materials. However, several other materials, such as oil or emulsions that the skin can absorb, alcohol-based mixtures that can evaporate with minimal residue, and many plastics can also meet these criteria. Furthermore, semi-solid gels based on alcohol, oils, or similar other liquids or thin layers of plastics with good ultrasound transmittance and matching to soft tissue can replace silicone or hydrogels in many instances where features such as "solid but conforming" may be required.

In addition, the presence of meshes or thin sheets of metal, doping with metal and metal oxides, etc., can generally be aberrating to the ultrasound field but can be used if specific spatial scales (such as thickness or mesh wire diameter) are kept below the wavelength of ultrasound; spacings in the mesh above wavelength; or the average density, speed of sound, or impedance of a volume of material at the wavelength scale matches that of soft-tissue. Examples of this concept can include, without limitation, magnetic nanoparticle-doped gels, damp sponges and membranes, thermos or electrically manipulable gels, and photosensitive resins. If meeting the acoustic matching requirements, they can easily replace instances of "silicone" or "hydrogel" mentioned.

Fluid Bag

Applying ultrasound well from a relatively flat and stiff transducer or transducer array to the head can address two physical issues. One is the macroscopic curvature of the skull. The other is the smaller-scale anatomical structures such as hair, dimples, pimples, and other features of the local skin. Either of these can lead to air gaps or other decoupling of the ultrasound from the head, causing potentially uncorrectable aberrations or loss of ultrasound transmission to the skull or head.

In an embodiment, the attachment puck 120 comprises multiple parts or layers to enhance usability and uses a fluid bag. Flexible fluid bags can adapt to the macroscopic curvature of the head or skull and the smaller-scale structures such as hair, etc.

Figure 2:
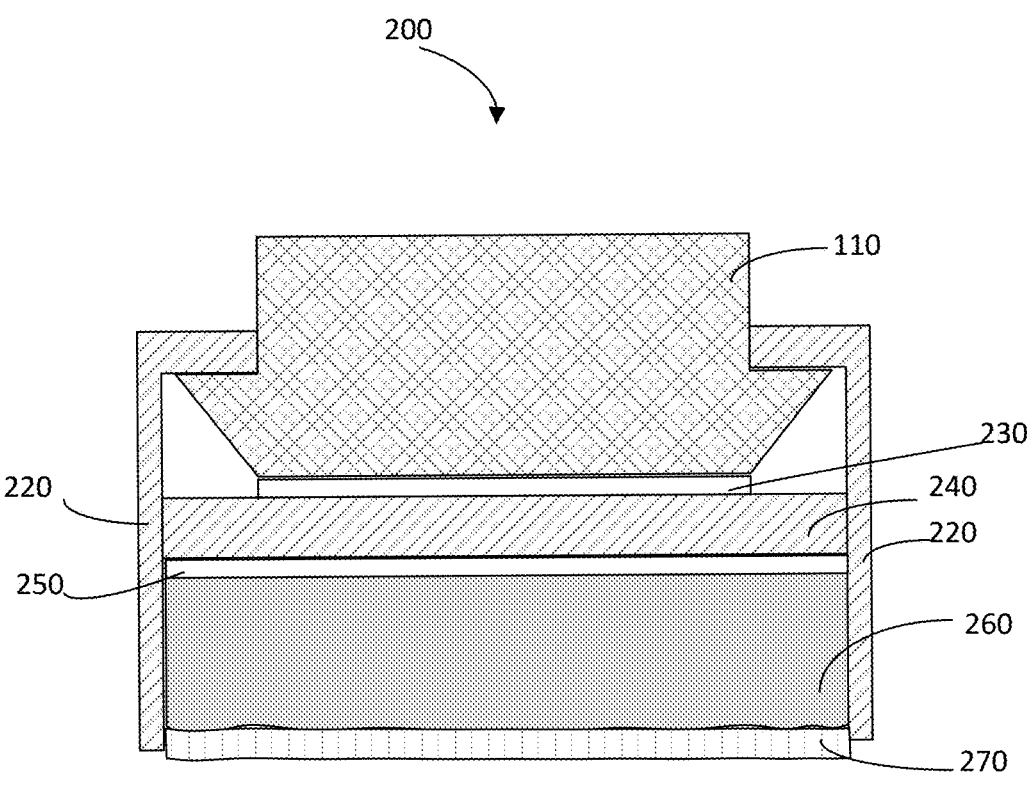
FIG. 2 is an example transducer coupling system using fluid bags according to various embodiments.

FIG. 2 shows one example of a transducer coupling apparatus 200 implementation using fluid bags. Referring to FIG. 2, transducer coupling apparatus 200 can include:

An outer shell 220 that can clip on (130) or Snap-On (135) to the holder unit 110, typically made of plastic or similar material and provides some rigidity to the whole structure.

A soft silicone or adhesive layer 230 in contact with holder unit 110

An ultrasound transmitting solid layer 240 that is acoustically matched for soft tissue. For example, a 3 mm thick LDPE cut to the shape of the holder unit 110 or its transducer (115) portion. Solid layer 240 is critical for alignment to the transducer 115.

An interfacing layer 250 made of soft silicone or adhesive. Layer 250 is used to attach the fluid bag. The fluid bag can contain, without limitation, one or more of a liquid, a gel, a hydrogel, or another interfacing material that aids an interface with the head.

A water or fluid bag 260 that is ultrasound transmitting. The bag is made of flexible but tear-resistant material (plastic) and filled with water. Any ultrasound-transmitting liquid can be used. In an embodiment, bag 260 has support membranes on the side or can be attached to the outer shell 220 on the sides, so it is not entirely shapeless.

The final skin interfacing layer 270. This can be made of soft silicone or solid or partially molten hydrogels, for example, to optimize the final coupling of ultrasound to the skull even with smaller structures such as dimples and hair present. Interfacing layer 270 can use adhesive to prevent uncoupling from the head. In a different embodiment, a small amount of traditional ultrasound gel can also be used in contrast to a large amount typically utilized to interface a sizeable flat transducer or holder unit 110 with a curved skull.

In some embodiments, layers 230 or 240 may be skipped, for example. Layer 240 can also be part of the holder unit 110 or a less-frequently replaced protective component for the holder unit 110 (for example, replaced only one-tenth as often as the fluid bag or interfacing layer 270). Outer shell

220, in some examples, reaches only partially height-wise and be somewhat malleable or flexible. It is primarily used to ensure that the liquid bad does not slide around to the extent that the edges of the bag may interfere with the ultrasound beam path.

Membraned Hydrogel or Soaked Sponge Pucks 120

In an embodiment, the attachment puck 120 includes or consists of a highly malleable matrix of hydrogel or soaked sponge as the core, surrounded by a slightly water-permeable outer membrane that is tear resistant. In an embodiment, the hydrogel or sponge core is self-healing or does not need healing. The bulk of the material transmitting the ultrasound should conform to the larger-scale shape of the skull. It can not easily form tears, air gaps, and other pockets within the material that affect ultrasound transmission. Self-healing materials can further recover on their own given time or with the addition of heat solvent (water, alcohol, etc.) such that tears are filled up, and ultrasound transmission is as before. Beyond silicone or hydrogels, polyurea, repenetrable silicone gels, and very dense polymer gels with sufficient liquid content can also meet this criterion. Alternatively, those with high liquid filling (a kitchen sponge) can also meet such requirements. However, such materials that rely on having high absorption of water or other liquids can generally use an outer membrane to prevent dripping as they can have a relatively easy flow of water. Clay and clay-like materials can be used for the core as they have a broad range of water content during which they remain plastic and can be molded while maintaining shape.

While providing structure and tear resistance, the outer membrane can also critically regulate how much liquid is released to solve the problem of materials releasing too much liquid. The outer membrane slows down or limits the liquid released. The outer membrane is flexible but provides resistance to ripping. The core concept can be appreciated with a simple comparison. A large, yellow, soft sponge that one traditionally imagines as a sponge can carry water and transmit ultrasound quite well in various shapes as it is bent, provided that all air has been removed. However, if one places that on one's head, there is a significant dripping of liquids. Now consider placing such a soaked sponge in a windbreaker jacket or pants that is water-resistant but not fully water-proof. Upon reasonable pressure, the sponge can dampen the windbreaker to allow a reasonable liquid release sufficient for a good ultrasound coupling interface while preventing the liquid from fully running down the face. The key is sufficiently dampening the surface of the head to create a good ultrasound interface without a constant liquid flow.

Figures 3A, 3B, 3C, 3D:
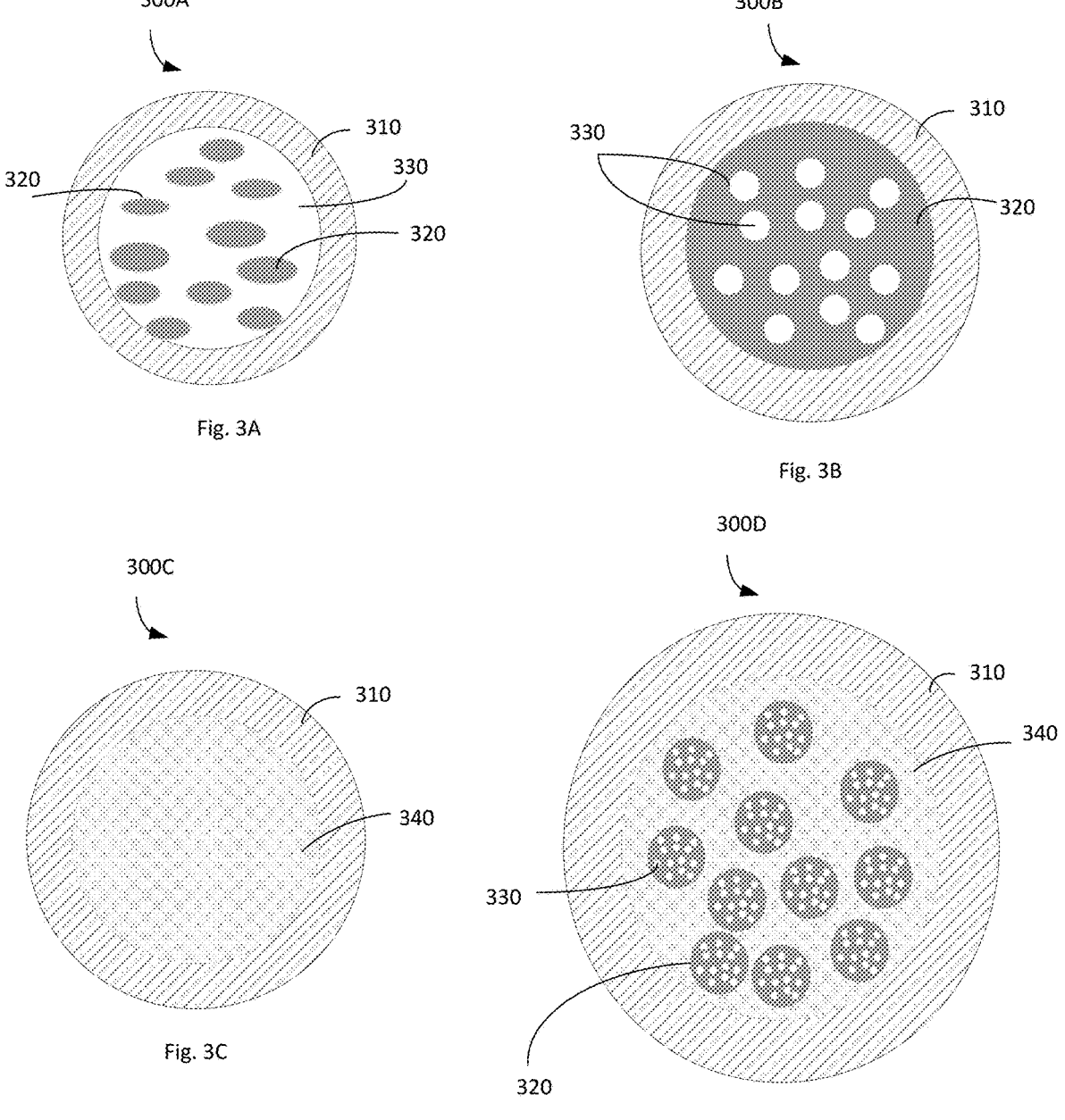
FIGS. 3A-3D show example implementations of attachment pucks using membraned hydrogels or soaked sponges according to various embodiments.

FIG. 3A, FIG. 3B, FIG. 3C, and FIG. 3D show example implementations of attachment pucks 120 using membraned hydrogels or soaked sponges. In these implementations, the membraned hydrogel or soaked sponge pucks replace fluid bags and the skin interfacing layer 270 described in FIG. 2. The attachment puck 120 can include an outer shell 220, adhesive layer 230, an ultrasound transmitting solid layer 240, and an interfacing layer 250 followed by the membraned hydrogel or soaked sponge layer. Note that this layer can be used as layer 260, 270, or both or in addition to them. FIG. 3A shows a soaked sponge layer 300A. Sponge layer 300A has an outer slightly permeable membrane 310, with one or more sponges 320 in its core. The sponge layer 300A is in contact with the head. When pressure is applied on the soaked sponges 320, they release water (or any other liquid, gel, or other fluid) to generate a skin-interfacing layer. The pressure can be applied using the springs 170 and screws 160 mentioned earlier. The outer slightly permeable membrane 310 slows down or limits the liquid released and prevents the liquid from running down on the face, eyes, ears, etc. In an embodiment, using ports and a syringe, pressure is applied. The ports and syringe can add additional interfacing water, liquid, or gel in a different embodiment. Sponge layer 300A is mostly sealed (there is no airflow). When pressure is removed, it can create negative pressure and suck up some of the released fluid such as a liquid or gel. A syringe and port can also be used to create the negative pressure. This reduces the amount of cleanup. The attachment puck can be soaked in water or liquid to prepare it for subsequent use.

FIG. 3B shows a soaked sponge layer 300B, which operates similarly to a soaked sponge layer 300A. In sponge layer 300B, the entire core is covered by a sponge 320 with one or more air pockets 330, which can fill up with water as in a regular sponge. FIG. 3C shows a membraned hydrogel layer 300C and operates similarly to the soaked sponge layer 300B. In the membraned hydrogel layer 300C, the core is occupied by hydrogel 340 and enclosed by the outer slightly permeable membrane 310. Hydrogel 340 has microscope holes as opposed to the sponge 320, which has macroscopic holes.

FIG. 3D shows layer 300D, which includes or consists of many sponges 320 in hydrogel 340 and enclosed by membrane 310. Layer 300D operates similarly to layer 300C. The sponges allow for extra capacity when layer 300D dries out, akin to a backup battery.

While the disclosure can focus on using hydrogel and water to soak or replenish the system as they are commonly used and easily understood, the same method can be used for other liquids, including oils, alcohols, or mixtures.

Gels and Physical Property-Tuned Gels

Gels and other fluids can have highly variable physical properties that external energy stimuli can tune. Such external energy stimuli include temperature, light (Photopolymers), pressure (non-Newtonian fluids), magnetic fields (magnetic doped particles such as magnetic nanoparticles (MNP)), electrical fields (statically charged (Electrorheological fluids)) etc.

Light can generate or break cross-links in polymers (for example, in 3D printing). Bidirectional (make and break) using two wavelengths of light or two separate energy modalities (temperature, electricity, light, or mechanical forces, including ultrasound) can further enhance usage and affect properties of the liquids and gels. For example, light sources like LED 175 can generate the required wavelengths. The fluids can generally Reversible (also called recurable or bidirectional) photopolymers can be made more solid or liquid by applying two different wavelengths of light. As is the case with many substances that go through such transitions (such as gentle warming of gelatin from a frozen state, the range of drying and wetness of clay), most such transitions do not occur in a way such that a material is "completely solid" or "completely liquid" and this ability to tune the "runniness" or fluidness is critical in the practical application of these materials for tFUS. Simple everyday examples of such materials (at least with one direction of curing) can include 3D print resins and UV-cured adhesives.

Non-Newtonian fluids can change viscosity depending on the forces applied. Some thicken with shear, like corn starch in water. Some thin out, like wall paint. Some have a cutoff before they start flowing, like ketchup or mayonnaise. Putties can be made of inorganic materials, such as minerals, mixed in water. A fully organic example can include dough. Synthetic polymers such as polyvinyl alcohol (PVA), which can be cross-linked by borax) or visco-elastic polymers such as Polydimethylsiloxane (PDMS). External mechanical forces to change the viscosity of these materials can be applied via ultrasound or buzzers.

Some gels can use multiple energy modalities. A simple example can include a gel that can polymerized (and hence more viscous or solid and thus less runny) via light and then made liquid again via gentle heat that breaks those bonds.

Doped Pucks and Gels

In an embodiment, gels or pucks doped with MNP are used. Such MNPs can in some examples be made purely or partially of metals or metal oxides (traditional magnetic materials) or molecule-based magnets. Proteins that can act as magnets or form self-assembling shells around magnetic molecules can also be used. The goal is that magnetic forces pulling on the MNP can pull along the gel or other embedding material around them. The material's overall bulk acoustic impedance can match that of soft tissue to optimize ultrasound transmission. The interaction between the MNP and a gel or viscous gel can be such that the application of magnetic forces on the MNP can then be transmitted to the gel, effectively pulling the gel along when pulling MNPs. Strategically placed electromagnets, such as electromagnet 195, shown in FIG. 1, can act on the MNP-doped gels to push or pull the gel to and from the head. When the MNPs are metal or metal oxide-based, their density may make their implementation in simple water-based solutions difficult as the impedance (density×speed-of-sound) will likely be higher. However, a base, such as silicone or emulsions, with a lower speed of sound or density can be used. In an implementation, MNPs are functionalized to have cross-links or other interactions with the surrounding gel to reduce the number of MNPs that are utilized. For example, MNPs with saccharide attachments embedded in agarose or similar media allow MNPs to drag more gel and reduce the MNPs effectively utilized. MNPs in functionalized shells can be similarly used with these shells containing cross-links. The larger shells can reduce the effective density changes due to the MNP and increase the interaction with the surrounding media to pull more of the media. Such MNP-based gels can reduce the dripping and mess during application and provide a simple cleanup method. In addition, this recapturing can allow the system to be reused for several applications.

Figures 4A, 4B, 4C, 4D:
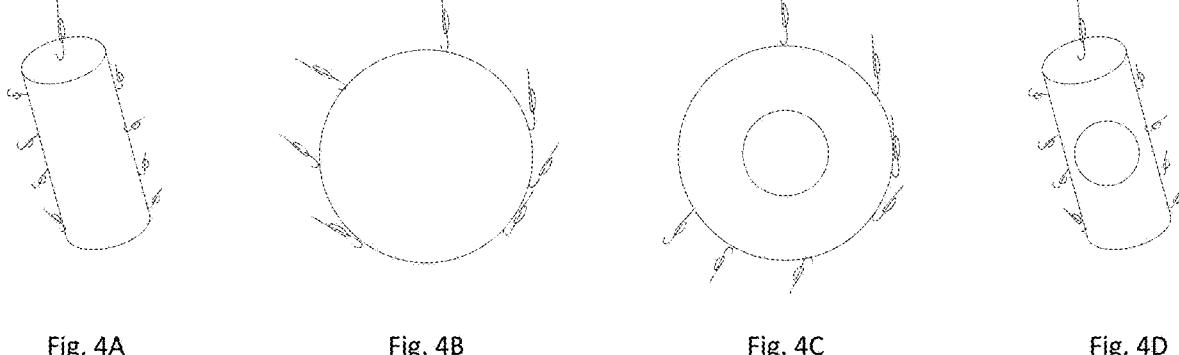
FIGS. 4A-4D show example implementations of magnetic nanoparticles in doped gels or pucks according to various embodiments.

In an implementation, MNPs are functionalized to have cross-links or other interactions with the surrounding gel to reduce the number of MNPs utilized. For example, MNPs with saccharide attachments embedded in agarose or similar media allow MNPs to drag more gel and reduce the MNPs needed or utilized effectively. FIGS. 4A-4D show example implementations of magnetic nanoparticles in doped gels or pucks. FIG. 4A shows an example of a magnetic nanorod, and FIG. 4B shows an example of a magnetic nanosphere. FIG. 4C and FIG. 4D show examples of magnetic nanoshells. FIG. 4C shows an example of MNPs in a spherical nanoshell, and FIG. 4D shows an example of MNPs in a rod nanoshell. MNPs in functionalized shells can be similarly used with these shells containing cross-links. The larger shells can reduce the effective density changes due to the MNP and increase the interaction with the surrounding media to pull more of the media. Such MNP-based gels can reduce the dripping and mess during application and provide a simple cleanup method. In addition, this recapturing can allow the system to be reused for several applications.

Similarly, electrorheological fluids (fluids with statically charged particles) can be used, especially those designed with weaker electric fields (<10V/mm). Electrodes 185 and Mesh 190 can generate the voltage gradient or electric field.

Besides safety, several parameters and properties of physical property-tuned gels and fluids can be considered and utilized by the system for modifications to system components such as heating elements, physical actuators, and other controls for use in a tFUS system application:

Thermo-responsiveness, temperature that the material starts melting, whether the material uses refrigeration such that it is taken out of a refrigerator for use, whether the material generally utilizes light heating (e.g., at or below 52-66 degrees Celsius) to melt, whether the material uses heating or cooling that remains on or just before or at the time of application, and similarly whether the material uses heating or cooling during or at the end of application, whether the material involves hydrophilic or hydrophobic change to temperature (to absorb and release liquids or water) to form the skin-interfacing layer, temperature-dependence of water-absorption capacity of the material (such as how juices come out when meat is cooked and how it can be reabsorbed when the steak rests), how conforming to shapes the material is at the small scale vs large scale, softness, runniness, and ability to withstand tears, stickiness to hair and head vs within itself, low stickiness relative to other materials but high stickiness relative to self is good for cleaning and self-healing, degree to which the material withstands ripping and tearing, whether the material "self-heal" after rips and tears, whether the material is a jamlike substance, whether the material is a jelly like substance, whether the material is self-healing gels which can be very different as compared to a standard liquid in practical use, whether the structure has cross-links that help maintain shape or increase viscosity and the ability to "pull off hair/head more cleanly" compared to just liquids (One notable difference from non-self-healing gels is that even if a physical disruption breaks these cross-links, they can re-form autonomously or perhaps with simple methods such as heating or adding water and subsequent drying, this is notable as liquids or self-healing gels can prevent air gaps and other physical discontinuities from forming, as these discontinuities can lead to significant ultrasound aberrations), whether the material be reheated and reused even if there are tears, other rheological and/or thixotropic properties such as "how quickly should they be wiped off for cleaning" and similar speed or force considerations.

Method for Liquids, Gels, and Physical Property-Tuned Gels

Figure 5:
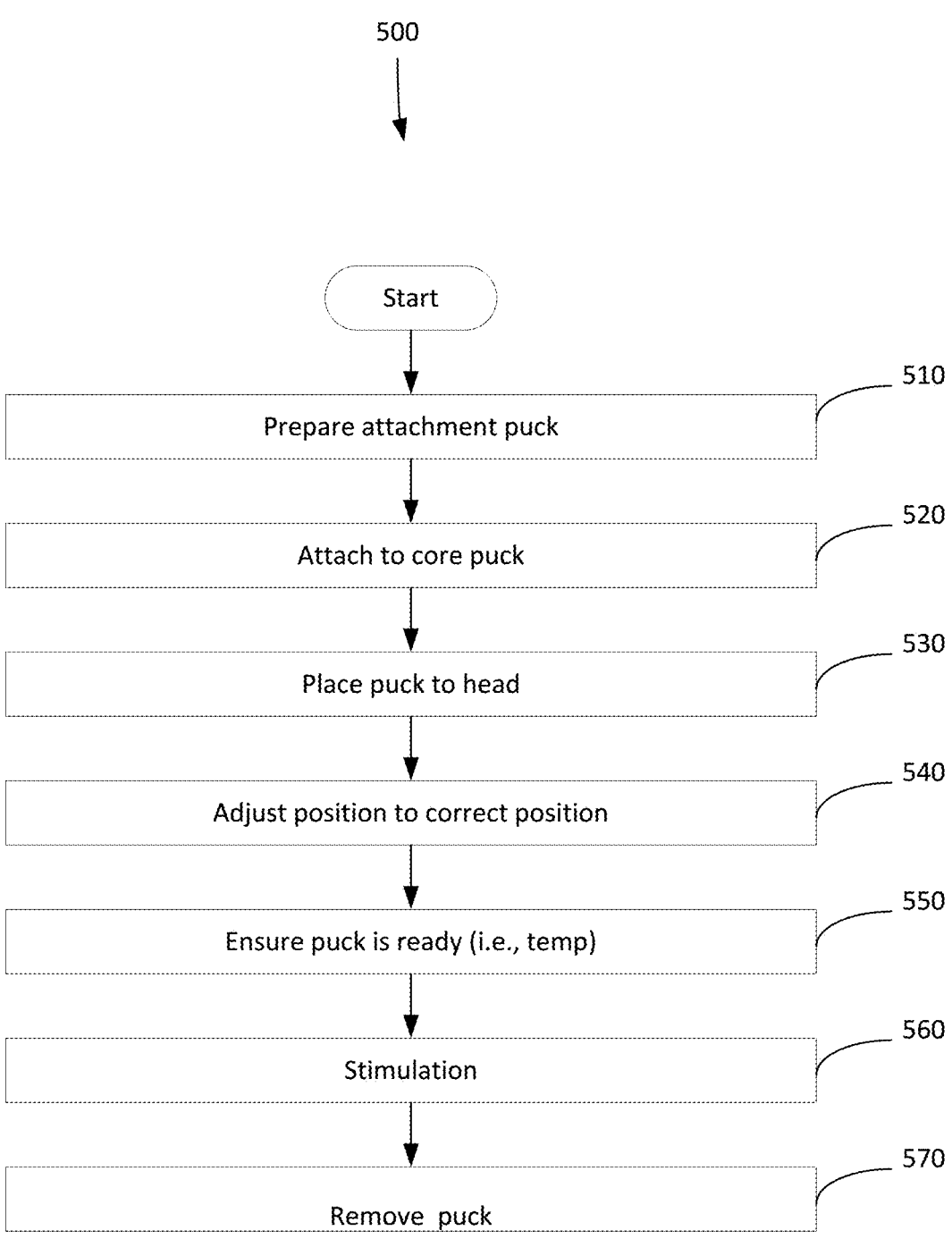
FIG. 5 shows an example flowchart performed by the components described according to various embodiments.

FIG. 5 shows an example flowchart 500 according to some embodiments. Although a flowchart or method can describe the operations as a sequential process, the operations can be performed concurrently. In addition, the order of the operations can be re-arranged. Flowchart 500 can be performed using the pucks described.

In operation 510, the attachment puck 120 is prepared. For example, a Thermo-responsive puck (for example, attachment puck 120 including or consisting of a gasket 140 in a mold, with molten hydrogel) is brought to the correct temperature (−15° C. or 5° C.) by placing it in a refrigerator, freezer, etc. For thermo-responsive attachment puck 120 that uses Peltier cooling, this operation can be skipped. If the puck uses a liquid or gel bag 260, the bag is inspected, and adhesive tape (for example, layer 220 or layer 270) is applied. The membrane or sponge layer (layer 300A, 300B, 300C, or 300D) is soaked in water or hydrogel for membraned hydrogels and soaked sponge-based attachment pucks 120.

In operation 520, the attachment puck is attached to holder unit 110. This can be done using latch 130, snap-fit 135, screws 160, or adhesive 230. For thermo-responsive pucks that use Peltier cooling, the puck is brought to the correct temperature (−15° C. or 5° C.). For MNP-doped gels or pucks, electromagnets 195 are set to "high" strength. For electrorheological fluids-based pucks, the fluid is subject to an appropriate electric field (for example, using electrodes 190). For photopolymers-based gels or pucks, the gel is treated with light of the correct wavelength using an appropriate light source, such as LEDs 175, to help solidify. For non-Newtonian fluids-based pucks, the fluid is subjected to a mechanical force using ultrasound transducers or buzzers to reduce viscosity or help solidify.

At operation 530, the transducer coupling apparatus (100A, 100B, 100C, or 200) is positioned on the patient's (or subject) head at an appropriate location. The puck can be secured with a double-sided adhesive (layer 270 or layer 150). Pressure can be applied to the puck to ensure that coupling fluid or gel is released from the attachment puck. For example, the pressure is applied using springs 170 and screws 160 to release gel or liquid from puck 120. The liquid or gel can be released from layers 300A, 300B, 300C, or 300D. A small amount of ultrasound gel can be used for better coupling.

At operation 540, using neuronavigation or other appropriate techniques, the puck's position is adjusted to ensure that stimulation or modulation waveforms can target the correct anatomy. For MNP-doped gels or pucks, electromagnets 195 are turned off or set to "weak" to allow the puck to conform to the skull's curvature and other smaller-scale anatomical structures. A display device (e.g., a screen on the holder device or another device) and/or LEDs on the holder device or a client device can provide visual neuro-navigational indicators that indicate holder positioning information including which direction and orientation to move the tFUS and EEG holder. LEDs can be shaped like arrows and show how to move the system(s). Neuro-navigational aids can include markers and indicators of various types. For example, neuro-navigational aids can include reflective beads or strips, as well as Light Emitting Diodes (LEDs) and other special markers that the overall system can detect using Light Detection and Ranging (LIDAR) and cameras. The neuro-navigational aids can be used with cameras or similar imaging systems to register the spatial location and orientation of the tFUS and EEG system on the subject's head. The special location and orientation can be associated with coupling of ultrasound and/or EEG. As a result, the imaging systems can be used to guide placement of the holder unit to increase ultrasound coupling and EEG coupling. A client device (such as a mobile device or a computer device), or the holder device can receive neuro-navigational detection data from a LIDAR device or a camera device. The neuro-navigational detection data can indicate a detection of the neuro-navigational aids relative to a head of a subject. The device can include an application that identifies a spatial location and orientation of the tFUS and EEG system relative to the head of the subject based on the neuro-navigational detection data. The device can also use the neuro-navigational detection data to identify characteristics of the head of the subject such as size and shape of the head. This head shape can include one or more three dimensional shapes corresponding to the subject's overall head shape. In one implementation, a smartphone-based app with an embedded camera is used to guide the placement of the tFUS and/or EEG coupling assembly. As a visual aid, the coupling assembly can activate multi-colored LEDs as feedback to indicate the correct and incorrect placement of both ultrasound and EEG components. A display device (e.g., a screen on the coupling assembly or a client device) and/or LEDs on the coupling assembly or another device can provide visual neuro-navigational indicators that indicate holder positioning information including which direction and orientation to move the coupling assembly. LEDs can be shaped like arrows and show how to move the system(s). In one implementation, two different sets of LEDs (spatially separated) are used to indicate the correct placement of the ultrasound and EEG, such as a left-right or up-down pair. A different set of LEDs (or other visual indicators such as user interface elements on a display device) can also indicate the coupling quality of the ultrasound and EEG. Similarly, LEDs can indicate the system's electrical or ultrasonic recording noise levels. A LIDAR system (can be internal or external to the coupling assembly) can be used to guide the placement. An internal LIDAR system with an external mirror, a camera, or a smartphone can guide the subject to place the coupling assembly. In another implementation, the coupling assembly includes magnetic sensors or magnets that can be turned on and off to help alignment or spatial-registration.

At operation 550, it is ensured that the coupling assembly unit or puck is ready for activation of ultrasound and/or EEG components. If the gel in the puck is solidified, it is allowed to liquefy to conform to the skull's curvature and other smaller-scale anatomical structures. The components of the coupling assembly unit can perform measurements with various sensors to detect whether the gel or liquid is at a predetermined consistency, and/or whether the gel or liquid is at a predetermined temperature pre-associated with that gel or liquid (e.g., indicative of a predetermined consistency). For thermo-responsive pucks, the gel is heated using body temperature, built-in heating elements (Mesh 190), or an external heating source (hair dryer). Other stimuli, like light, etc., are used as required. For MNP-doped gels or pucks, electromagnets 195 are set to "medium."

At operation 560, ultrasound stimulates, inhibits, or modulates target anatomical structures.

At operation 570, after stimulation or neuromodulation (treatment) is complete, holder unit 110 is prepared for removal. Negative pressure is created by loosening screws 160. This can help suck some of the gel/liquid that was used for coupling for an easier cleanup. In addition, other operations like the heating being turned off, cooling being turned on, electromagnet 195 being set to "high," etc., are performed. The ultrasound transducer coupling apparatus (100A, 100B, 100C, or 200) is removed.

The core operations are to make the coupling materials more solid or liquid at the correct stages to make handling easier, to allow better coupling, and to reduce dripping during tFUS application or cleanup. For some gels, such as MNP-doped gels, during cleaning, the system can include a magnetic field strength high enough to pull along molecules, not just hold them in place or prevent running. Such operations can be pre-preparation (soaking, putting in a freezer, etc.), active (heaters, Peltier, magnets) to make more or less solid on the subject's head, that such things can be reversed on the head, use of vacuums or negative pressure (sponges that are no longer squeezed) can be used to help soak up or clean up further, etc. These operations can be performed in any number of ways or orders, and a coupling puck can also use more than one energy modality for this solid/liquid or viscosity control.

Vacuum Application

Figure 6:
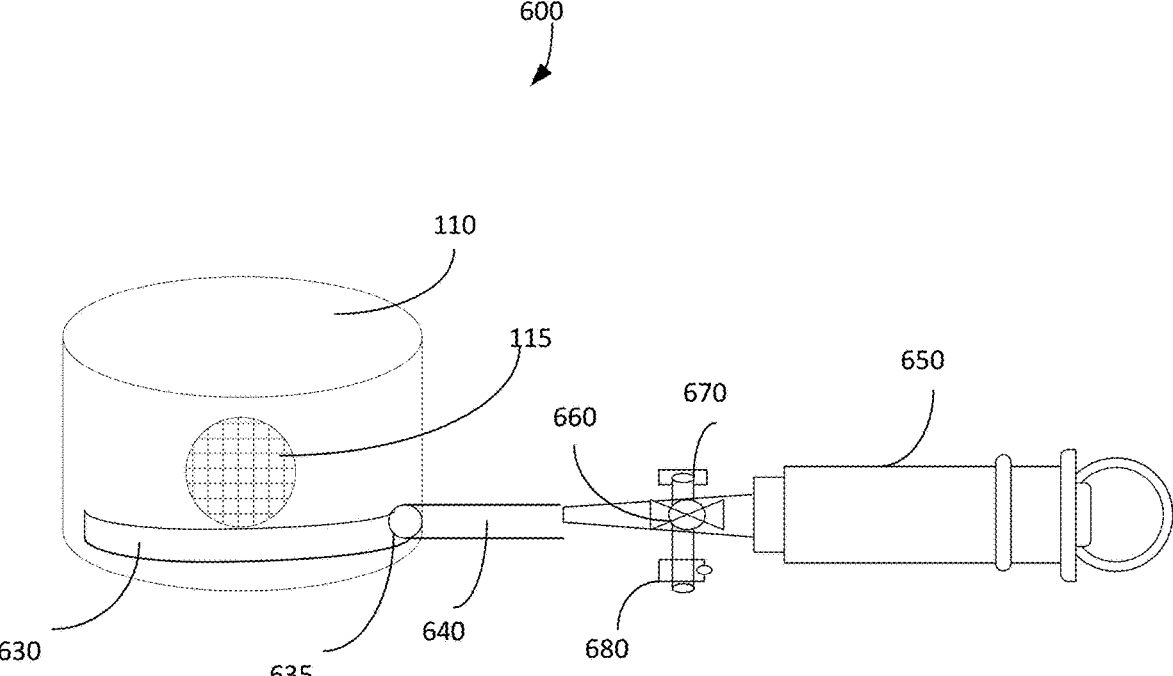
FIG. 6 shows an example transducer coupling system that can connect with an external vacuum according to various embodiments.

In an embodiment, an external vacuum source such as a syringe is used to apply gel or cleanup. FIG. 6 shows an example coupling apparatus 600 that can connect with an external vacuum. The coupling apparatus 600 is similar to transducer coupling apparatus 100A, 100B, 100C, and 200, with the difference that it includes a fillable chamber 630 with a port 640. Referring to FIG. 6, coupling apparatus 600 includes holder unit 110 with transducer 115 (or transducer array). Underneath the array 115 is a fillable chamber 630 with a port 635. Port 635 can be used to fill chamber 630 or to create a vacuum.

In an implementation, chamber 630 is a part of attachment puck 120. Attachment puck 120 includes O-ring 140, attachment layer 150, etc., as described earlier. Tube 640 is attached to port 635. A syringe 650 is attached to tube 640 via multi-way valve 660. One end of the valve is capped with a pressure cap 660. The other end is attached to pinch valve 680 (or a more straightforward mechanism that can be used to adjust airflow resistance). Syringe 650 with the multi-way valve 660 can be used to fill the chamber 630, create a positive pressure, or create a vacuum. The attachment puck 120 includes channels that allow for gel to ooze onto the head.

A positive pressure can force the gel onto the head through the channel. A vacuum can not only hold the gel in place, prevent leaks, and aid in cleaning after ultrasound application, but it can also clean the chamber and reduce the chance of mold build-up. The syringe at various time points can be filled with gel, water, or other cleaning solution, air, or a combination. As an example, a syringe can initially be filled with gel. It is used to fill out the coupling apparatus 600. At the end of the ultrasound application, the syringe may be pulled back, sucking in both gel and air. The syringe can be disconnected, emptied, filled with water, and reattached using the valves. The system, including the hair, can be rinsed through by pushing the syringe. The chamber can then be emptied by pulling on the syringe. An air-filled syringe can pressurize and depressurize the coupling apparatus 600 during treatment and can, along with the pinch valve, offer more straightforward control of suction or constant pressure of gel.

Figure 7:
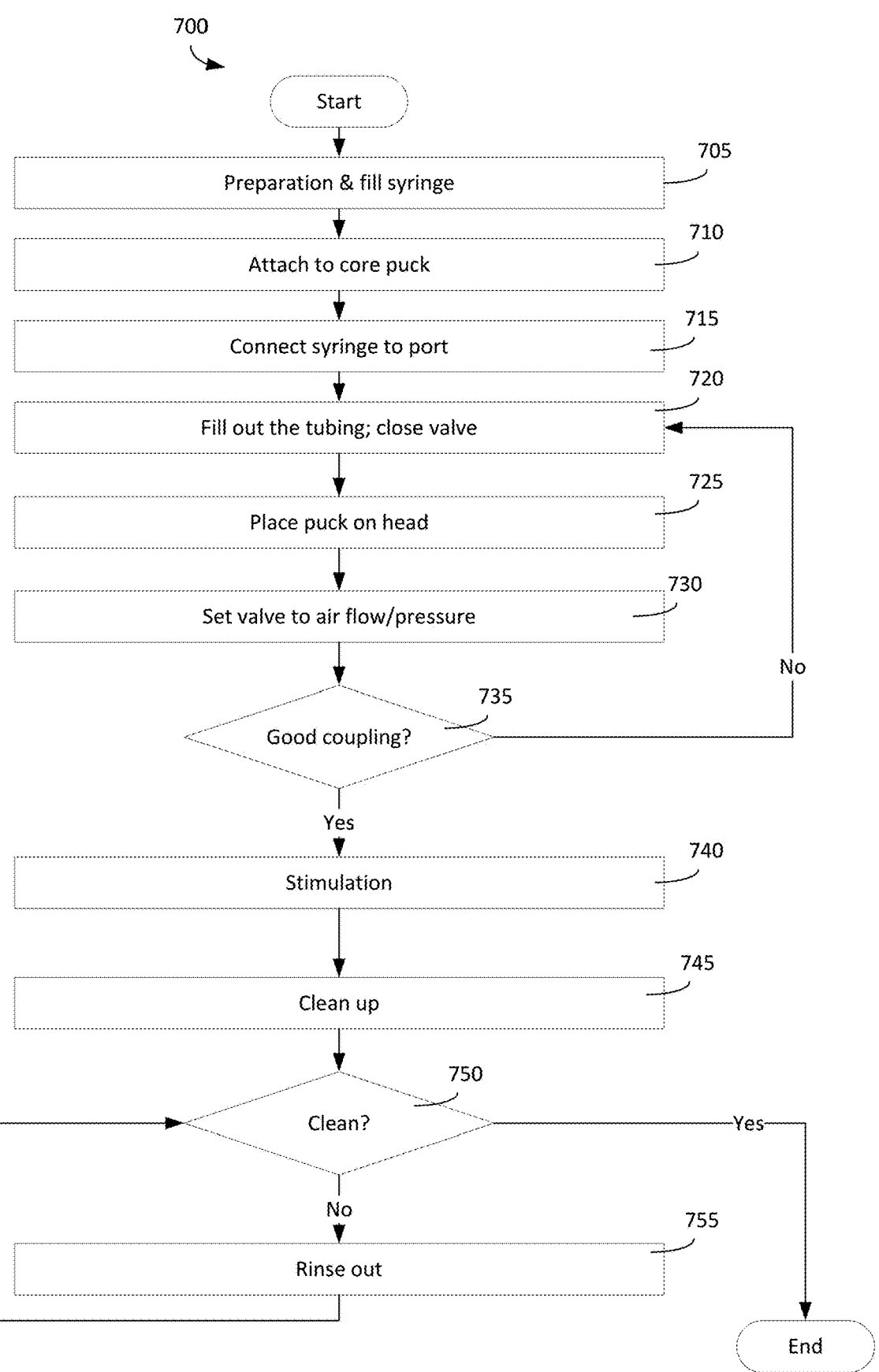
FIG. 7 shows an example flowchart that can be used for applying gel or cleanup according to various embodiments.

FIG. 7 shows an example flowchart 700 that can be used for applying gel or cleanup. Flowchart 700 can be used with coupling apparatus 600. Referring to FIG. 7, in operation 705, preparation is performed. It can include adding adhesives (attaching to head or holder unit 110) and similar operations. Syringe 650 is filled with gel. As the volume of chamber 630 is known, syringe 650 can be filled with the required volume of gel or liquid.

In operation 710, attachment puck 120 is attached to the holder unit 110 using a clasp, snap-fit, screws, or adhesive to form a US an/dor EEG coupling assembly unit.

In operation, syringe 650 is connected to port 640 via a suitable tube.

In operation 720, chamber 630 and tube 640 are filled with gel. Valve 660 is closed.

In operation 725, coupling apparatus 600 is placed on the patient's (subject) head. The placement of puck 600 is adjusted using neuronavigation or other techniques so that the puck can stimulate the targeted anatomy.

In operation 730, valve 660 is set for airflow or pressure. This causes the gel to ooze onto the head from channels within the attachment puck 620.

In operation 735, the quality of coupling of coupling apparatus 600 with the head is checked. This can be done using impedance measurements. If there is good coupling, valve 660 is closed and the next operation is Operation 740. If the coupling is not good, the following operation is Operation 720.

In operation 740, the patient is stimulated (inhibited or neuromodulated).

In operation 745, cleanup is performed. First, valve 660 is set to syringe 650, and a vacuum is created by pulling on the syringe. The gel from chamber 630 is evacuated into syringe 650. Valve 660 is closed and syringe 650 is emptied. The vacuum can also help gel from the patient's head if the negative pressure is strong enough.

In operation 750, it is determined if chamber 630 is clean. If it is determined that chamber 630 is not clean, the following operation is Operation 755.

In operation 755, the chamber 630 is rinsed out with water. It is critical for the O-ring to be mess-free.

Customized Attachment Pucks

In an embodiment, attachment pucks 120 that confirm to a subject or patient's head are used. Customized attachment pucks 120 can account for the skull's curvature. Such a customized attachment puck 120 can in some examples still utilize gel for interfacing to the head, but the volume can be decreased relative to standard uncustomized pucks since the volume of the gap between the head and the puck can be reduced. In addition, any sealing (gasket) can work much more effectively due to the customization. Thin layers of interfacing silicone or hydrogels that do not drip can also be used due to the conformation to their head shape provided by the customized attachment layer. In addition, such a customized attachment puck can make targeting easier as the "right fit" location can be much more specific than trying to align and angle a flat surface (say, a generic puck or transducer surface) to the skull.

In an implementation, 3D printing is used for creating customized attachment pucks 120. The 3D printing be used for generating molds, removable frames, supporting shapes, or even the base silicone or similar portion of the puck that transmits the ultrasound itself. Several techniques can be used to measure a subject's skull or head. LIDAR can be used to create a detailed curvature and location "map" of the skull. Magnetic Resonance Imaging (MRI) can generate a very accurate representation of the skull's location and curvature. In a low-cost method, a pin screen device with displacement sensors mounted on the back to measure displacement of a plurality of pins of the pin screen to create curvature information. In a moderate-cost implementation, a webcam or phone camera with an app can be used, perhaps with a physical accessory such as a pen or headbands with LEDs to be seen by the camera. The pen can locate anatomical markers such as nose bridges, eyes, ears, and the temple. It can also be used to trace the shape of the skull, even through the hair. Headbands and similar can be fitted on the head as well, and they can also include stretch and position sensors embedded to record geometry. Such systems can be shipped to a new user for accurate head measurements and then returned for reuse with other new customers or those wanting to readjust their fit.

Figure 8:
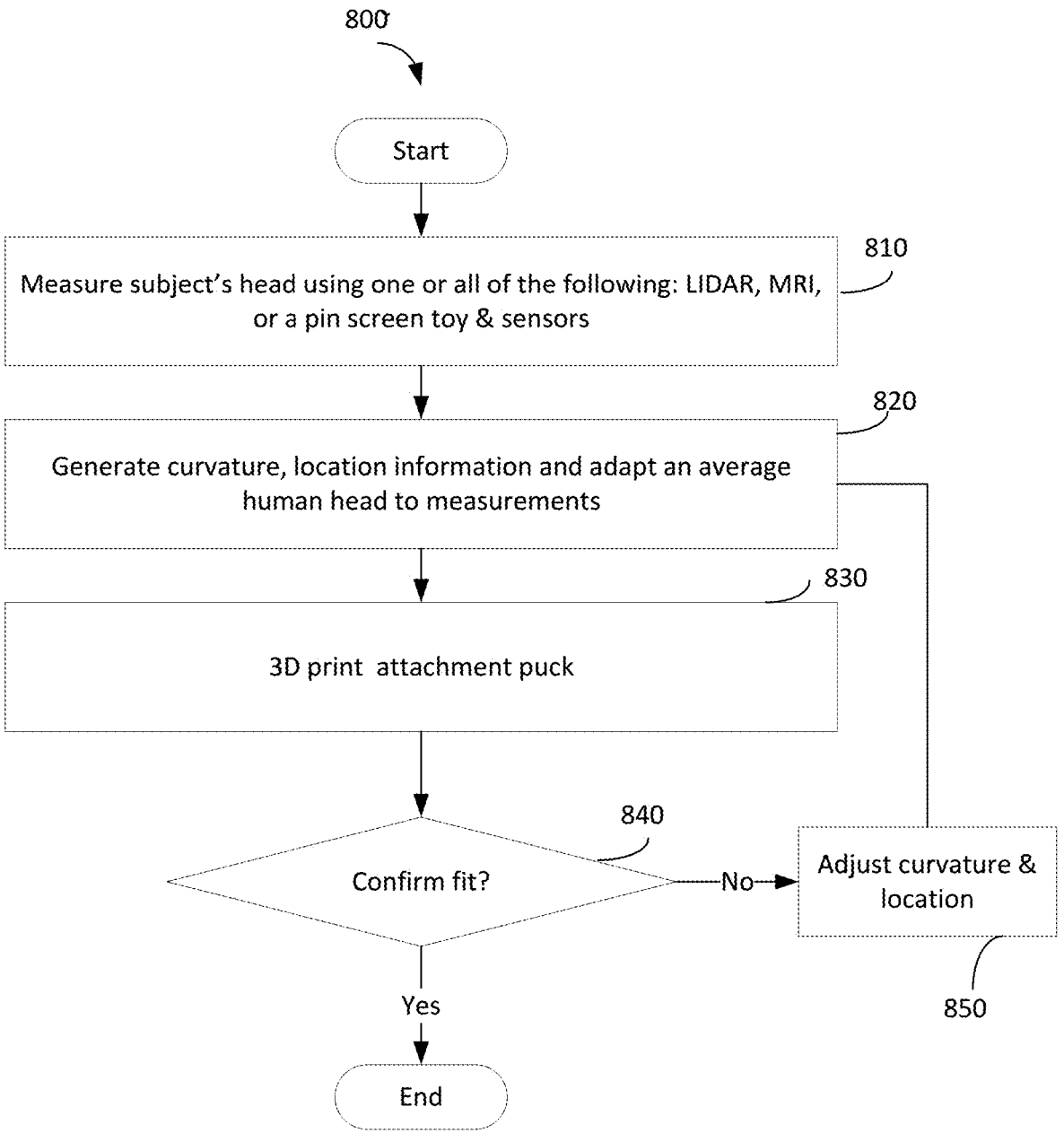
FIG. 8 shows an example method for creating customized attachment pucks according to various embodiments.

FIG. 8 shows an example method for creating customized attachment pucks 120. Referring to FIG. 8, in operation 810, the subject's head is measured. LIDAR, MRI, or a pin-screen device (e.g., similar in some respects to a pin screen toy device) & sensors can create data on the subject skull curvature and location information. MRI creates the most accurate data but is more involved and costly. LIDAR is now available on smartphones and can be used.

In operation 820, the curvature and location information of the subject's skull is generated from the measurement performed in Operation 810. Average (or generic/nonspecific) human head shapes and brain maps are adapted to the local measurements. For example, data comprising the local measurements and overall head size measurements from operation 810 can be used to modify data defining an average or generic human head shape to generate customized head shape data. In one example, the average human head shape data can be scaled to match a sizing measurement from operation 810 to generate customized head shape data. The average (and/or customized) head shape data can also be modified to have a different shape in one or more portions of the head that are measured in operation 810 to generate customized head shape data.

In operation 830, a customized attachment puck 120 is 3D printed. In some examples, the customized attachment puck 120 can include a shape that matches the customized head shape data, for example, corresponding to a particular portion of a head of a subject. In other situations, the customized attachment puck 120 can be generated based on a set of parameters generated using the customized head shape data. The set of parameters can include, without limitation, average, mean, maximum, minimum, and other measures of curvature for all of a portion of the customized head shape can be calculated. One or more of these parameters can be used to generate a customized attachment puck 120 for printing.

In optional operation 840, the fit of the customized attachment puck is evaluated. If the fit is not good, the following operation is Operation 850.

In operation 850, the curvature and location data are adjusted based on feedback.

In an embodiment, customized attachment pucks 120 can be combined with features described in other pucks and gels described previously (100A-C, 200, used with external vacuum, combined with gels with physical properties).

At least one technical advantage of the disclosed techniques relative to the prior art is that, with the disclosed techniques, multiple components and layers can provide improved sealing and compliance in relation to gaps between the device and skull geometry as well as smaller-scale features such as dimples, hair, etc. For example, an attachment puck can detachably attach to a holder unit, so that the interface components can be fresher than examples that do not include a detachable puck system that include attachment pucks 120. This can improve coupling, reduce mess, and provide easier clean-up relative to existing technologies. Gaskets or O-rings are used to improve the sealing with the head in some implementations. Pressure and vacuum can improve coupling in association with examples including gasket and O-ring implementations. These technical advantages provide one or more technological advancements over prior art approaches.

Aspects of the subject matter described herein are set out in the following numbered clauses.

1. In some embodiments, a system comprises a holder unit comprising one or more ultrasound transducers, and an attachment puck comprising at least one layer.

2. The system of clause 1, wherein the at least one layer is configured to interface with a head.

3. The system of clauses 1 or 2, wherein the attachment puck comprises a curve concave to the head.

4. The system of any of clauses 1-3, wherein at least a portion of the attachment puck comprises a circular shape, a rectangular shape, an elliptical shape, a curved shape, or a combination of multiple shapes.

5. The system of any of clauses 1-4, further comprising an electroencephalogram (EEG) component, wherein the EEG component is utilized to monitor efficacy of an ultrasound treatment provided using the one or more ultrasound transducers.

6. The system of any of clauses 1-5, wherein at least one of the holder unit, or the attachment puck comprises a mesh located relative to a liquid or gel.

7. The system of any of clauses 1-6, wherein the mesh affects a property of a liquid or gel by at least one of thermal conduction, generating heat, or generating an electrical field.

8. The system of any of clauses 1-7, wherein a shape of at least a portion of the attachment puck matches a predetermined shape of the head.

9. The system of any of clauses 1-8, wherein the attachment puck comprises at least one of an O-ring or a gasket that provides at least a partial seal to the head that prevents at least a portion of a liquid or gel from escaping an area defined based at least in part by the O-ring or the gasket.

10. The system of any of clauses 1-9, further comprising at least one electromagnet that affects magnetic nanoparticles in a liquid or gel.

11. The system of any of clauses 1-10, wherein the magnetic nanoparticles comprise at least one of spherical nanoparticles, rod-shaped nanoparticles, spherical nanoshell nanoparticles, or rod-shaped nanoshell nanoparticles.

12. The system of any of clauses 1-11, wherein the attachment puck comprises at least one of a liquid, a gel, or a hydrogel.

13. The system of any of clauses 1-12, wherein the liquid, the gel, or the hydrogel of the attachment puck are responsive to one or more energy stimuli comprising at least one of temperature, light, pressure, magnetic field, or electric field.

14. The system of any of clauses 1-13, wherein the attachment puck comprises channels that deliver the at least one of the liquid, the gel, or the hydrogel to the head.

15. The system of any of clauses 1-14, wherein the attachment puck comprises a fluid bag that contains the at least one of the liquid, the gel, or the hydrogel.

16. The system of any of clauses 1-15, wherein the fluid bag is ultrasound transmitting, flexible, and tear-resistant fluid bag with optional support membranes on the sides so the bag are attachable to the outer shell.

17. The system of any of clauses 1-16, wherein attachment puck further comprises an outer shell that provides rigidity, a silicone or adhesive layer in contact with the holder unit, an ultrasound transmitting solid layer that is acoustically matched to soft tissue, and a head interfacing layer comprising at least one of soft silicone, hydrogel, or adhesive to attach the fluid bag.

18. The system of any of clauses 1-17, wherein the fluid bag comprises one or more support membranes that are configured for attachment to the outer shell.

19. The system of any of clauses 1-18, wherein at least one of the holder unit, or the attachment puck comprises a thermal regulation system the regulates a temperature of a liquid or gel based on a target temperature for the liquid or gel.

20. The system of any of clauses 1-19, wherein the thermal regulation system comprises a Peltier cooler.

21. The system of any of clauses 1-20, wherein at least one of the holder unit, or the attachment puck comprises one or more light emitting diodes (LEDs).

22. The system of any of clauses 1-21, wherein the LEDs comprise at least one of indicator neuro-navigational indicator LEDs, neuro-navigational marker LEDs, or LEDs that are controlled to affect a property of a liquid or gel.

23. The system of any of clauses 1-22, wherein the attachment puck is detachably attached to the holder unit using at least one of a clasp, a snap-fit, screws, or double-sided adhesives.

24. The system of any of clauses 1-23, wherein the attachment puck is reusable or refurbishable.

25. The system of any of clauses 1-24, further comprising at least one of screws or springs, wherein an operation of the at least one of the screws or the springs causes a controlled pressure that applies a liquid or gel to the head.

26. The system of any of clauses 1-25, wherein another operation of the at least one of the screws or springs causes a negative pressure that removes at least a portion of the liquid or gel from the head.

27. The system of any of clauses 1-26, wherein the attachment puck further comprises a slightly permeable outer membrane that is tear resistant and slows liquid flow.

28. The system of any of clauses 1-27, wherein the permeable outer membrane contains a hydrogel comprises microscopic holes.

29. The system of any of clauses 1-28, wherein the slightly permeable outer membrane contains one or more sponges and air gaps between the one or more sponges, wherein when pressure is applied, a liquid held in the one or more sponges oozes out to fill the air gaps.

30. The system of any of clauses 1-29, wherein the one or more sponges comprise air pocket within holes within the one or more sponges.

31. In some embodiments, a method comprises configuring or preparing an attachment puck to interface with a head, attaching the attachment puck to a holder unit comprising at least one of one or more ultrasound transducers, or one or more electroencephalogram (EEG) electrodes to form a coupling assembly unit, and positioning the coupling assembly unit on a head.

32. The method of clause 31, further comprising providing one or more neuro-navigational indicators that indicate an adjusted position for the coupling assembly unit relative to the head.

33. The method of clauses 31 or 32, further comprising identifying that the assembly unit is ready for activation of the at least one of the one or more ultrasound transducers, or the one or more electroencephalogram (EEG) electrodes, wherein a component of the assembly unit measures at least one of a temperature or a material consistency to identify that the assembly unit is ready for activation, and activating the at least one of the one or more ultrasound transducers, or the one or more electroencephalogram (EEG) electrodes.

34. In some embodiments, a method comprises preparing a syringe, wherein preparing the syringe comprises filling the syringe with a liquid or gel, attaching the syringe to an assembly comprising a holder unit and an attachment puck, setting a valve of the syringe to a positive pressure setting that provides positive pressure that causes the liquid or gel to flow from the attachment puck to the head.

35. The method of clause 34, further comprising setting the valve of the syringe to a setting that enables negative pressure that causes at least a portion of the liquid or gel to be removed from the head.

36. The method of clauses 34 or 35, wherein the negative pressure is providing by operating or manipulating the syringe.

37. In some embodiments, a method comprises measuring a head of a subject using at least one of a Light Detection and Ranging (LIDAR) device, a Magnetic Resonance Imaging (MRI) device, or a pin screen device comprising displacement sensors, generating measured curvature and location data based at least in part on at least one measurement identified using the at least one of the LIDAR device, the MRI device, or the pin screen device, modifying data defining a generic human shape based at least in part on the measured curvature and location information to generate customized head shape data, generating a customized attachment puck shape based on the customized head shape data, and printing, using a printing device, a customized attachment puck corresponding to the customized attachment puck shape.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments can be embodied as a system, method or computer program product. Accordingly, aspects of the present disclosure can take the form of an entirely hardware embodiment, an entirely software embodiment (including firmware, resident software, microcode, etc.) or an embodiment combining software and hardware aspects that can all generally be referred to herein as a "module," a "system," or a "computer." In addition, any hardware and/or software technique, process, function, component, engine, module, or system described in the present disclosure can be implemented as a circuit or set of circuits. Furthermore, aspects of the present disclosure can take the form of a computer program product embodied in one or more computer readable medium(s) having computer readable program code embodied thereon.

Any combination of one or more computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions can be provided to a processor of a general purpose computer, special purpose computer, or other programmable data processing apparatus to produce a machine. The instructions, when executed via the processor of the computer or other programmable data processing apparatus, enable the implementation of the functions/acts specified in the flowchart and/or block diagram block or blocks. Such processors can be, without limitation, general purpose processors, special-purpose processors, application-specific processors, or field-programmable gate arrays.

The flowchart and block diagrams in the figures illustrate the architecture, functionality, and operation of possible implementations of systems, methods and computer program products according to various embodiments of the present disclosure. In this regard, each block in the flowchart or block diagrams can represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure can be devised without departing from the basic scope thereof, and the scope thereof is determined by the claims that follow.

What is claimed is:

1. A system comprising:
   a holder unit comprising one or more ultrasound transducers; and
   an attachment puck comprising at least one layer, wherein at least one of the holder unit or the attachment puck comprises one or more light emitting diodes (LEDs) and wherein the LEDs comprise at least one of: indicator neuro-navigational indicator LEDs, neuro-navigational marker LEDs, or LEDs that are controlled to affect a property of a liquid or gel, wherein the attachment puck further comprises a permeable outer membrane that is tear resistant and slows liquid flow, a hydrogel comprising microscopic holes, and one or more sponges comprising one or more air gaps between the one or more sponges, wherein when pressure is applied, a liquid held in the one or more sponges oozes out to fill the air gaps.

2. The system of claim 1, wherein the at least one layer is configured to interface with a head.

3. The system of claim 2, wherein the attachment puck comprises a curve concave to the head.

4. The system of claim 1, wherein at least a portion of the attachment puck comprises a circular shape, a rectangular shape, an elliptical shape, a curved shape, or a combination of multiple shapes.

5. The system of claim 1, further comprising an electroencephalogram (EEG) component, wherein the EEG component is utilized to monitor efficacy of an ultrasound treatment provided using the one or more ultrasound transducers.

6. The system of claim 1, wherein at least one of the holder unit, or the attachment puck comprises a mesh located relative to a liquid or gel.

7. The system of claim 6, wherein the mesh affects a property of a liquid or gel by at least one of: thermal conduction, generating heat, or generating an electrical field.

8. The system of claim 2, wherein a shape of at least a portion of the attachment puck matches a predetermined shape of the head.

9. The system of claim 1, wherein the attachment puck comprises at least one of an O-ring or a gasket that provides at least a partial seal to a head that prevents at least a portion of a liquid or gel from escaping an area defined based at least in part by the O-ring or the gasket.

10. The system of claim 1, further comprising at least one electromagnet that affects magnetic nanoparticles in a liquid or gel.

11. The system of claim 10, wherein the magnetic nanoparticles comprise at least one of: spherical nanoparticles, rod-shaped nanoparticles, spherical nanoshell nanoparticles, or rod-shaped nanoshell nanoparticles.

12. The system of claim 1, wherein the attachment puck comprises at least one of: a liquid, a gel, or a hydrogel.

13. The system of claim 12, wherein the liquid, the gel, or the hydrogel of the attachment puck are responsive to one or more energy stimuli comprising at least one of: temperature, light, pressure, magnetic field, or electric field.

14. The system of claim 12, wherein the attachment puck comprises channels that deliver the at least one of: the liquid, the gel, or the hydrogel to a head.

15. The system of claim 13, wherein the attachment puck comprises a fluid bag that contains the at least one of: the liquid, the gel, or the hydrogel.

16. The system of claim 15, wherein the fluid bag is ultrasound transmitting or flexible.

17. The system of claim 15, wherein the attachment puck further comprises:

an outer shell that provides rigidity;

a silicone or adhesive layer in contact with the holder unit;

an ultrasound transmitting solid layer that is acoustically matched to soft tissue; and a head interfacing layer comprising at least one of soft silicone, hydrogel, or adhesive to attach the fluid bag.

18. The system of claim 17, wherein the fluid bag comprises one or more support membranes that are configured for attachment to the outer shell.

19. The system of claim 1, wherein at least one of the holder unit, or the attachment puck comprises a thermal regulation system that regulates a temperature of a liquid or gel based on a target temperature for the liquid or gel.

20. The system of claim 19, wherein the thermal regulation system comprises a Peltier cooler.

21. The system of claim 1, wherein the attachment puck is detachably attached to the holder unit using at least one of: a clasp, a snap-fit, screws, or double-sided adhesives.

22. The system of claim 1, wherein the attachment puck is reusable or refurbishable.

23. The system of claim 1, further comprising at least one of screws or springs, wherein an operation of the at least one of the screws or the springs causes a controlled pressure that applies a liquid or gel to a head.

24. The system of claim 23, wherein another operation of the at least one of the screws or springs causes a negative pressure that removes at least a portion of the liquid or gel from the head.

25. The system of claim 1, wherein the one or more sponges comprise air pocket within holes within the one or more sponges.

* * * * *